United States Patent [19]

Kennis et al.

[11] Patent Number: 4,804,663

[45] Date of Patent: Feb. 14, 1989

[54] 3-PIPERIDINYL-SUBSTITUTED 1,2-BENZISOXAZOLES AND 1,2-BENZISOTHIAZOLES

[75] Inventors: Ludo E. J. Kennis, Turnhout; Jan Vandenberk, Beerse, both of Belgium

[73] Assignee: Janssen Pharmaceutica N.V., Beerse, Belgium

[21] Appl. No.: 826,517

[22] Filed: Feb. 5, 1986

Related U.S. Application Data

[63] Continuation-in-part of Ser. No. 717,067, Mar. 27, 1985, abandoned.

[51] Int. Cl.[4] .................. C07D 471/04; C07D 513/04; C07D 239/96; A61K 31/505
[52] U.S. Cl. ................................. 514/258; 514/224.2; 514/259; 544/54; 544/278; 544/282; 544/284; 546/225; 546/226; 546/232
[58] Field of Search ................. 544/278, 282, 284, 54; 514/259, 258, 224.2

[56] References Cited

U.S. PATENT DOCUMENTS

| | | | |
|---|---|---|---|
| 4,128,641 | 12/1978 | Itil | 514/250 |
| 4,335,127 | 6/1982 | Vandenberk et al. | 424/251 |
| 4,337,261 | 6/1982 | Shutske et al. | 548/241 |
| 4,342,870 | 8/1982 | Kennis et al. | 544/282 |
| 4,352,811 | 10/1982 | Strupczewski et al. | 424/267 |
| 4,443,451 | 4/1984 | Kennis et al. | 424/251 |
| 4,458,076 | 7/1984 | Strupczewski et al. | 546/199 |
| 4,485,107 | 11/1984 | Kennis et al. | 424/251 |
| 4,529,727 | 7/1985 | Kennis et al. | 514/224.2 |
| 4,665,075 | 5/1987 | Vandenberk et al. | 544/284 |
| 4,689,330 | 8/1987 | Janssens et al. | 514/258 |
| 4,737,500 | 4/1988 | Sorg | 544/284 |

Primary Examiner—Donald G. Daus
Assistant Examiner—Emily Bernhardt

[57] ABSTRACT

3-Piperdinyl-1,2-benzisothiazoles and 3-piperidinyl-1,2-benzisoxazoles and their pharmaceutically acceptable acid addition salts having useful antipsychotic properties and being useful in the treatment of a variety of complaints in which serotonin release is of predominant importance.

18 Claims, No Drawings

3-PIPERIDINYL-SUBSTITUTED 1,2-BENZISOXAZOLES AND 1,2-BENZISOTHIAZOLES

CROSS-REFERENCE TO RELATED APPLICATIONS

This is a continuation-in-part of our copending application Ser. No. 717,067, filed Mar. 27, 1985, now abandoned.

BACKGROUND OF THE INVENTION

In U.S. Pat. No. 4,352,811 and U.S. Pat. No. 4,458,076 there are described 3-piperidinyl-1,2-benzisoxazoles and 3-piperidinyl-1,2-benzisothiazoles having antipsychotic and analgesic properties.

The compounds of the present invention differ from those prior art compounds by their substitution on the 1-position of the piperidine moiety.

DESCRIPTION OF THE PREFERRED EMBODIMENTS

The present invention is concerned with 1,2-benzazoles having the formula

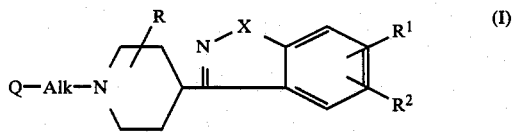

and the pharmaceutically acceptable acid addition salts thereof, wherein

R is hydrogen or $C_{1-6}$ alkyl;
$R^1$ and $R^2$ are each independently members selected from the group consisting of hydrogen, halo, hydroxy, $C_{1-6}$ alkyloxy and $C_{1-6}$ alkyl;
X is O or S;
Alk is $C_{1-4}$ alkanediyl; and
Q is a radical of formula

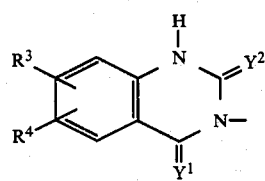

wherein $Y^1$ and $Y^2$ are each independently O or S;
$R^3$ is a member selected from the group consisting of hydrogen, halo, $C_{1-6}$ alkyl, $C_{1-6}$ alkyloxy, trifluoromethyl, nitro, cyano, hydroxy, ($C_{1-10}$ alkylcarbonyl)oxy, amino, mono- and di($C_{1-6}$ alkyl)amino, ($C_{1-10}$ alkylcarbonyl)amino, phenylmethoxy and azido;
$R^4$ is hydrogen or halo; or a radical of formula

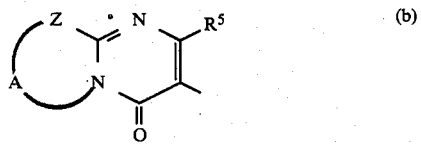

wherein $R^5$ is hydrogen or $C_{1-6}$ alkyl;
Z is —S—, —CH$_2$— or —CR$^6$=CR$^7$—; said $R^6$ and $R^7$ being each independently hydrogen or $C_{1-6}$ alkyl; and
A is a bivalent radical —CH$_2$—CH$_2$—, —CH$_2$—CH$_2$—CH$_2$— or —CR$^8$=CR$^9$—, said $R^8$ and $R^9$ being each independently hydrogen, halo, amino or $C_{1-6}$ alkyl.

In the foregoing definitions the term halo is generic to fluoro, chloro, bromo and iodo; "$C_{1-6}$ alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like; "$C_{1-4}$ alkanediyl" is meant to include bivalent straight or branch chained alkanediyl radicals having from 1 to 4 carbon atoms, such as, for example, methylene, ethylene, propylene, butylene and the like; and "$C_{1-10}$ alkyl" is meant to include $C_{1-6}$ alkyl radicals, as defined hereinabove, and the higher homologs thereof having from 7 to 10 carbon atoms, such as, for example, heptyl, nonyl and the like;

Preferred compounds within the invention are those wherein Q is a radical of formula (a) wherein $R^3$ is hydrogen, halo, $C_{1-6}$ alkyl, $C_{1-6}$ alkyloxy, trifluoromethyl, hydroxy, amino or azido and $R^4$ is hydrogen; or Q is a radical of formula (b) wherein $R^5$ is $C_{1-6}$ alkyl and A is a bivalent radical —CH$_2$—CH$_2$—, —CH$_2$—CH$_2$—CH$_2$— or —CR$^8$=CR$^9$— wherein $R^8$ and $R^9$ are each independently hydrogen or $C_{1-6}$ alkyl.

Particularly preferred compounds are those preferred compounds wherein R is hydrogen, $R^1$ is hydrogen or halo and $R^2$ is hydrogen, halo, hydroxy or $C_{1-6}$ alkyloxy.

More particularly preferred compounds are those particularly preferred compounds wherein Q is a radical of formula (a) wherein $R^3$ is hydrogen, halo or methyl and $Y^1$ is O; or Q is a radical of formula (b) wherein —Z—A— is —S—CH$_2$—CH$_2$—, —S—(CH$_2$)$_3$—, —S—CR$^8$=CR$^9$— wherein $R^8$ and $R^9$ are each independently hydrogen or methyl, —CH=CH—CR$^8$=CR$^9$— wherein $R^8$ and $R^9$ are each independently hydrogen or methyl, or —CH$_2$—CH$_2$—CH$_2$—CH$_2$—.

Especially preferred compounds are those more particularly preferred compounds wherein $R^1$ is hydrogen, and $R^2$ is hydrogen, halo, hydroxy or methoxy.

The most preferred compounds are selected from the group consisting of 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one and 3-[2-[4-(6-fluoro-1,2-benzisoxazol-3-yl)-1-piperidinyl]ethyl]-2-methyl-4H-pyrido[1,2-a]pyrimidin-4-one and the pharmaceutically acceptable acid addition salts thereof.

The compounds of formula (I) can generally be prepared by reacting an appropriate reactive ester of formula (II) with an appropriately substituted piperidine of formula (III). In the reactive ester (II) W represents a reactive ester residue such as, for example, halo, e.g., chloro, bromo or iodo, or a sulfonyloxy group, e.g. methylsulfonyloxy, (4-methylphenyl)sulfonyloxy and the like.

Q—Alk—W +

(II)

-continued

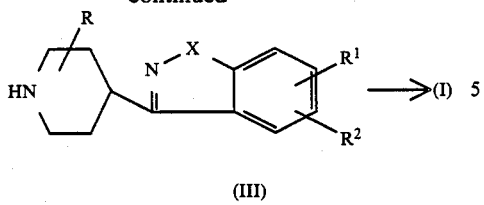

(III)

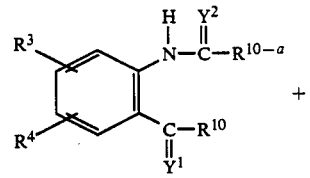

(IV-b)

The reaction of (II) with (III) can conveniently be conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1′-oxybisethane, tetrahydrofuran and the like; N,N-dimethylformamide (DMF); N,N-dimethylacetamide (DMA); nitrobenzene; 1-methyl-2-pyrrolidinone; and the like. The addition of an appropriate base such as, for example, an alkali or an earth alkaline metal carbonate, hydrogen carbonate, hydroxide, alkoxide or hydride, e.g., sodium carbonate, sodium hydrogen carbonate, potassium carbonate, sodium hydroxide, sodium methoxide, sodium hydride and the like, or an organic base such as, for example, a tertiary amine, e.g., N,N-diethylethanamine, N-(1-methylethyl)-2-propanamine, 4-ethylmorpholine and the like may be utilized to pick up the acid which is liberated during the course of the reaction. In some circumstances the addition of a iodide salt, preferably an alkali metal iodide, is appropriate. Somewhat elevated temperatures may enhance the rate of the reaction.

The compounds of formula (I) may also be prepared following art-known procedures for preparing compounds containing radicals of formula Q within their structure.

For example, the compounds of formula (I) wherein Q is a radical of formula (a), said compounds being represented by the formula (I-a), can be prepared by cyclizing an appropriate 2-amino-benzamide or 2-aminobenzenethioamide of formula (IV-a) with urea or thiourea.

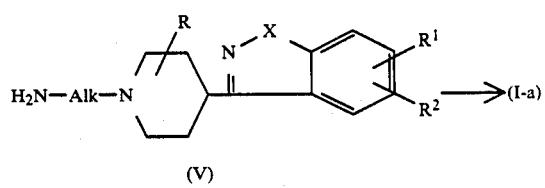

(V)

or by cyclizing an isocyanate or isothiocyanate of formula (IV-c) with a primary amine of formula (V).

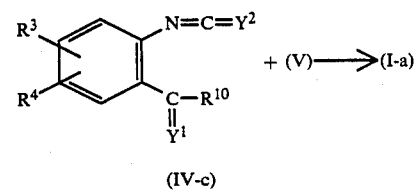

(IV-c)

The said cyclization-reactions are conveniently conducted by stirring and, if desired, heating the reactants together, optionally in a suitable reaction-inert solvent having a relatively high boiling point such as aliphatic and aromatic hydrocarbons, e.g. petroleum ether, dimethylbenzene and the like.

In the foregoing reaction schemes $R^{10}$ and $R^{10\text{-}a}$ each independently represent an appropriate leaving group such as, for example, $C_{1-6}$ alkyloxy, amino, and mono- and di($C_{1-6}$ alkyl)amino.

The compounds of formula (I) wherein Q is a radical of formula (b), said compounds being represented by the formula (I-b), can be prepared following art-known cyclizing procedures for preparing pyrimidin-4-ones

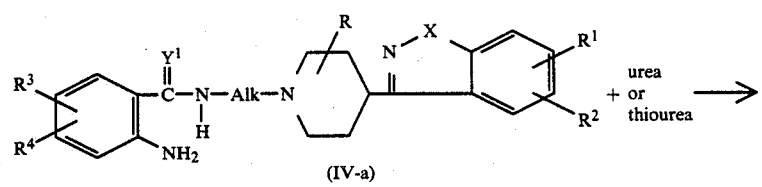

(IV-a)

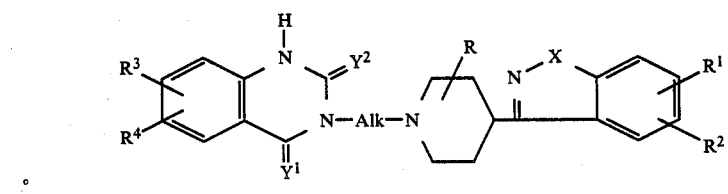

(I-a)

The compounds of formula (I-a) can also be prepared by cyclizing an appropriate intermediate of formula (IV-b) with an amine of formula (V)

such as, for example, by reacting an amine of formula (VI) with a cyclizing agent of formula (VII) or by cyclizing a reagent of formula (VIII) with an amine of formula (IX).

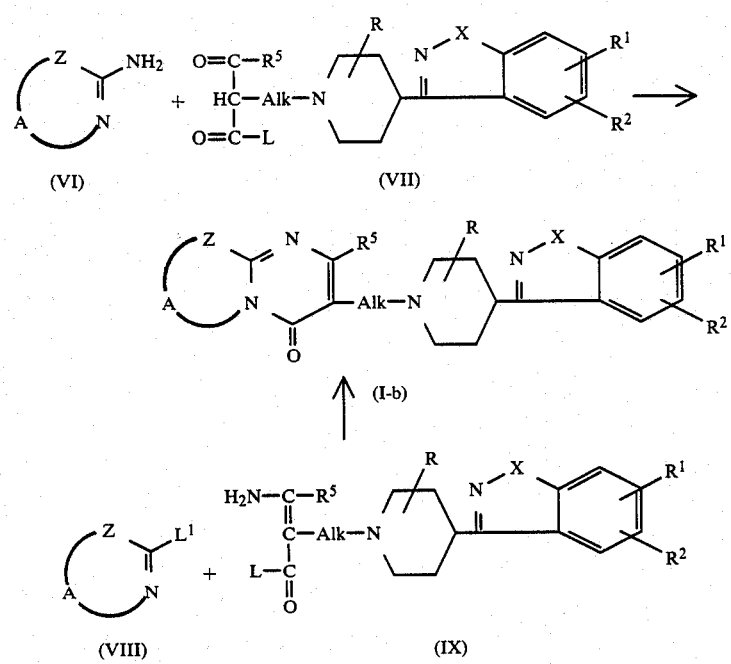

The said cyclization reactions may generally be carried out by stirring the reactants together, if desired, in the presence of a suitable reaction-inert solvent such as, for example, an aliphatic-, alicyclic- or aromatic hydrocarbon, e.g., hexane, cyclohexane, benzene and the like; pyridine; N,N-dimethylformamide and the like amides. Elevated temperatures may be appropriate to enhance the reaction-rate. In some cases it may be preferable to carry out the reaction at the reflux temperature of the reaction mixture.

In the foregoing reaction schemes L and $L^1$ each independently represent an appropriate leaving group such as, for example, $(C_{1-6}$ alkyl)oxy, hydroxy, halo, amino, mono- and di($C_{1-6}$ alkyl)amino and the like.

Following the same cyclization procedure the compounds of formula (I-b) can also be prepared by cyclizing an intermediate of formula (IX) with a reagent of formula (X).

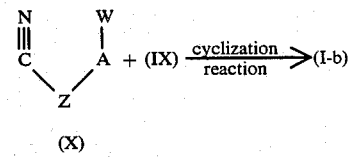

The compounds of formula (I-b) wherein Z is S, said compounds being represented by the formula (I-b-1), can also be prepared by cyclizing a 2-mercaptopyrimidinone of formula (XI) with a reagent of formula (XIII).

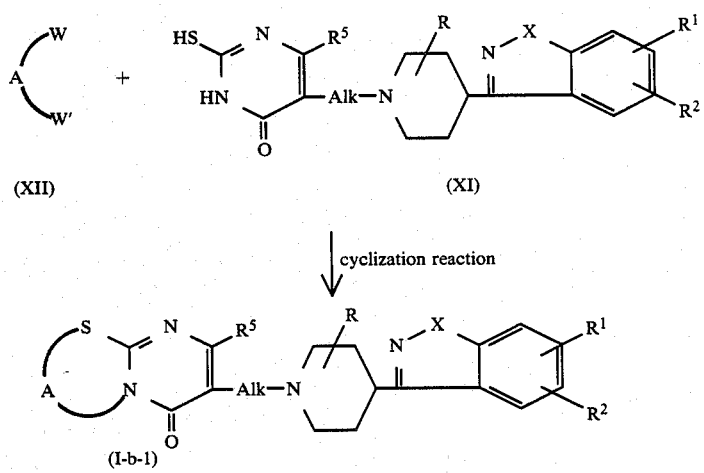

In (XII) W' has the same meaning as previously described for W.

The compounds of formula (I-b-1) wherein A is

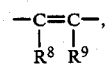

said compounds being represented by the formula (I-b-1-a), can also be prepared by cyclizing a 2-mercaptopyrimidinone of formula (XI) with a reagent of formula (XIII).

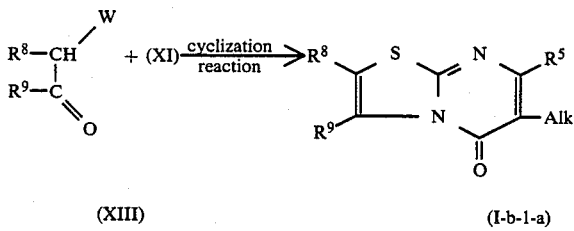

(XIII)    (I-b-1-a)

The cyclization reactions for preparing the compounds of formulae (I-b-1) and (I-b-1-a) may generally be carried out by stirring the reactants together, if desired, in the presence of a suitable reaction-inert solvent such as, for example, an aliphatic-, alicyclic- or aromatic hydrocarbon, e.g., hexane, cyclohexane, benzene and the like; pyridine; N,N-dimethylformamide and the like amides. Elevated temperatures may be appropriate to enhance the reaction-rate. In some cases it may be preferable to carry out the reaction at the reflux temperature of the reaction mixture.

The compounds of formula (I) may also be converted into each other following art-known functional group transformation procedures.

For example, the compounds of formula (I-a) wherein $R^3$ is amino, may be derived from the corresponding nitro-substituted quinazolines following art-known nitro-to-amine reduction procedures. A suitable nitro-to-amine reducing procedure is, for example, catalytic hydrogenation in a relatively polar solvent such as, for example, an alcohol, e.g. methanol or ethanol, in the presence of an appropriate catalyst, e.g. platinum-on-charcoal. In some cases it may be useful to add an appropriate catalyst poison, e.g. thiophene.

The compounds of formula (I-a) wherein $R^3$ is phenylmethoxy may be converted into compounds of formula (I-a) wherein $R^3$ is hydroxy following art-known catalytic hydrogenolysis procedures; the compounds of formula (I-a) wherein $R^3$ is amino or hydroxy may be converted into compounds of formula (I-a) wherein $R^3$ is ($C_{1-10}$ alkylcarbonyl)amino or ($C_{1-10}$ alkylcarbonyl)oxy respectively by reacting the former compounds with a suitable acylating agent, e.g. an acylhalide or an acid anhydride; the compounds of formula (I-a) wherein $R^3$ is an amino-group may be converted into compounds of formula (I-a) wherein $R^3$ is an azido-group by converting the amino-group into a diazonium group with nitrous acid or an appropriate alkali metal or earth alkaline metal thereof and subsequently converting the said diazonium group into an azide group with sodium azide or any other suitable alkali metal or earth alkaline metal azide.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic anc the like, the sulfuric acid, nitric acid, phosphoric acid and the like; or organic acids, such as, for example, acetic, propanoic, hydroacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

A number of intermediates and starting materials in the foregoing preparations are known compounds which may be prepared according to art-known methodologies of preparing said or similar compounds. For example, the intermediates of formula (III) and their preparations are described in U.S. Pat. Nos. 4,335,127; 4,342,870; 4,443,451; and 4,485,107. Other intermediates may be prepared according to art-known methodologies of preparing similar compounds and for some of them preparative methods are presented hereinafter.

The intermediates of formula (III) may generally be derived from a benzoylpiperidine of formula

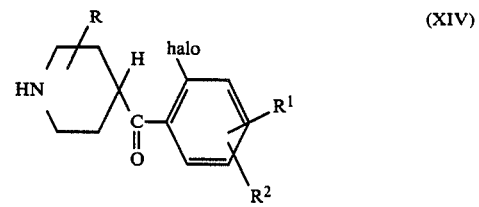

wherein halo is preferably fluoro, following art-known procedures, e.g. by reacting the benzoylpiperidine (XIV) with hydroxylamine and cyclizing the thus obtained oxime

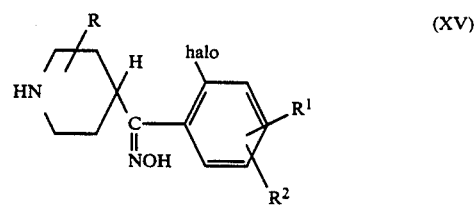

following art-known procedures, thus obtaining the intermediate of formula (III) wherein X is O, said intermediates being represented by the formula

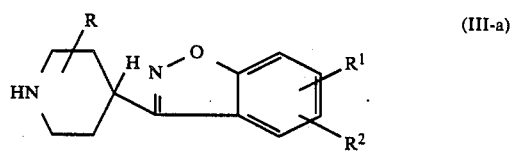

The intermediates of formula (III) wherein X is S, said intermediates being represented by the formula

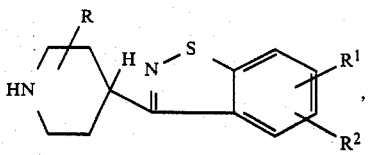

(III-b)

may be prepared following a procedure analogous to the procedure described in U.S. Pat. No. 4,458,076.

The compounds of formula (I) and the pharmaceutical acceptable acid addition salts thereof are potent antagonists of a series of neurotransmittors and as a result they have useful pharmacological properties. For example, the compounds of formula (I) and their pharmaceutically acceptable acid addition salts possess strong psychotic activity and antiserotonine activity.

Due to their pharmacological activities the compounds of formula (I) and their pharmaceutically acceptable acid addition salts can be used in the treatment of psychotic diseases and in the treatment of a variety of complaints in which serotonin release is of predominant importance such as, for example, in the blocking of serotonin-induced contractions of bronchial tissues and of blood vessels, arteries as well as veins. The subject compounds have also useful properties as sedating-, anxiolytic-, anti-agressive-, anti-stress-, muscular protectant- and cardiovascular protectant agents and, consequently, they are useful to protect warm-blooded animals, for example, in stress situations, e.g., during transport periods and the like situations. Additionally, the subject compounds are useful as protectors of endotoxine shocks and as antidiarrhoeals.

In view of their useful pharmacological properties, the subject compounds may be formulated into various pharmaceutical forms for administration purposes. To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoon-fuls and the like, and segregated multiples thereof.

In view of the usefulness of the subject compounds in the treatment of psychotic diseases it is evident that the present invention provides a method of treating warm-blooded animals suffering from psychotic diseases, said method comprising the systemic administration of a pharmaceutically effective amount of a compound of formula (I) or a pharmaceutically acceptable acid addition salt thereof in admixture with a pharmaceutical carrier. Those of skill in the treatment of psychotic diseases could easily determine the effective amount from the test results presented here. In general it is contemplated that an effective amount would be from 0.01 mg/kg to 4 mg/kg body weight, more preferably from 0.04 mg/kg to 2 mg/kg body weight.

The following examples are intented to illustrate and not to limit the scope of the present invention. Unless otherwise stated all parts therein are by weight and all temperatures are in the centigrade scale.

EXPERIMENTAL PART (A) Preparation of the intermediates

EXAMPLE 1

To a stirred mixture of 65 parts of 1,3-difluorobenzene, 130 parts of aluminium chloride and 195 parts of dichloromethane was added dropwise a solution of 95 parts of 1-acetyl-4-piperidine-carbonyl chloride in 65 parts of dichloromethane while cooling. Upon completion, stirring was continued for 3 hours at room temperature. The reaction mixture was poured into a mixture of crushed ice and hydrochloric acid. The product was extracted with dichloromethane. The organic layer was dried, filtered and evaporated, yielding 48 parts (36%) of 1-acetyl-4-(2,4-difluorobenzoyl)piperidine as a residue (intermediate 1).

A mixture of 48 parts of 1-acetyl-4-(2,4-difluorobenzoyl)-piperidine and 180 parts of a hydrochloric acid solution 6N was stirred and refluxed for 5 hours. The reaction mixture was evaporated and the residue was stirred in 2-propanol. The product was filtered off and dried, yielding 39 parts (83%) of (2,4-difluorophenyl)(4-piperidinyl)methanone hydrochloride (intermediate 2).

A mixture of 12 parts of (2,4-difluorophenyl)(4-piperidinyl)methanone hydrochloride, 12 parts of hydroxylamine hydrochloride and 120 parts of ethanol was stirred at room temperature and 10.5 parts of N,N-diethylenethanamine were added. The whole was stirred and refluxed for 3 hours. After cooling, the precipitated product was filtered off and dried, yielding 11 parts (100%) of (2,4-difluorophenyl)(4-piperidinyl)methanone, oxime (intermediate 3).

A mixture of 11 parts of (2,4-difluorophenyl)(4-piperidinyl)-methanone, oxime, 25 parts of potassium hydroxide and 25 parts of water was stirred and refluxed for 2 hours. The reaction mixture was cooled and extracted with methylbenzene. The extract was dried, filtered and evaporated. The residue was crystallized from petroleumether, yielding 6.8 parts of 6-fluoro-3-(4-piperidinyl)-1,2-benzisoxazole (intermediate 4).

EXAMPLE 2

A mixture of 50 parts of 2-thiazolamine, 76 parts of 3-acetyl-4,5-dihydro-2(3H)-furanone, 1.2 parts of concentrate hydrochloric acid and 270 parts of methylbenzene was stirred and refluxed for 2 hours using a water-separator. The reaction mixture was cooled and 340 parts of phosphoryl chloride were added at a temperature between 20° and 30° C. The whole was heated slowly to 100°–110° C. and stirring was continued for 2 hours at this temperature. The reaction mixture was evaporated and the residue was poured into a mixture of crushed ice and ammonium hydroxide. The product was extracted with trichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from a mixture of 2-propanol and 1,1'-oxybisethane, yielding 36 parts of 6-(2-chloroethyl)-7-methyl-5H-thiazolo[3,2-a]pyrimidin-5-one (intermediate 5).

EXAMPLE 3

A mixture of 30 parts of 4-hydroxy-2-mercapto-6-methyl-5-pyrimidineethanol, 25 parts of potassium carbonate, 270 parts of N,N-dimethylacetamide and 75 parts of water was stirred at room temperature and 36 parts of 1,3-dibromopropane were added at once: temperature rose to 50° C. The whole was stirred overnight at room temperature. The reaction mixture was evaporated and water was added to the residue. The solid product was washed with water and dried in vacuo at 100° C., yielding 21 parts (58%) of 3,4-dihydro-7-(2-hydroxyethyl)-8-methyl-2H,6H-pyrimido-[2,1-b][1,3]thiazin-6-one; mp. 155° C. (intermediate 6).

Following the same procedure and using equivalent amounts of the appropriate starting materials, there was also prepared: 2,3-dihydro-6-(2-hydroxyethyl)-7-methyl-5H-thiazolo[3,2-a]pyrimidin-5-one; mp. 148.7° C. (intermediate 7).

EXAMPLE 4

A mixture of 20 parts of 3,4-dihydro-7-(2-hydroxyethyl)-8-methyl-2H,6H-pyrimido[2,1-b][1,3]thiazin-6-one, 50 parts of acetic acid and 180 parts of a hydrobromic acid solution 67% in acetic acid was stirred and heated to reflux. Stirring was continued overnight at reflux temperature. The reaction mixture was evaporated and the solid residue was triturated in 2-propanone. The product was filtered off and dried, yielding 24 parts (100%) of 7-(2-bromoethyl)-3,4-dihydro-8-methyl-2H,6H-pyrimido[2,1-b][1,3]thiazin-6-one; monohydrobromide; mp. 215° C. (intermediate 8).

Following the same procedure and using equivalent amounts of the appropriate starting materials, there was also prepared: 6-(2-bromoethyl)-2,3-dihydro-7-methyl-5H-thiazolo[3,2-a]pyrimidin-5-one monohydrochloride; mp. 237.2° C. (intermediate 9).

(B) Preparation of the final compounds

EXAMPLE 5

A mixture of 5.3 parts of 3-(2-chloroethyl)-6,7,8,9-tetrahydro-2-methyl-4H-pyrido[1,2-a]pyrimidin-4-one monohydrochloride, 4.4 parts of 6-fluoro-3-(4-piperidinyl)-1,2-benzisoxazole, 8 parts of sodium carbonate, 0.1 parts of potassium iodide and 90 parts of N,N-dimethylformamide was stirred overnight at 85°–90° C. After cooling, the reaction mixture was poured into water. The product was filtered off and crystallized from a mixture of N,N-dimethylformamide and 2-propanol. The product was filtered off and dried, yielding 3.8 parts (46%) of 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one; mp. 170.0° C. (compound 1).

Following the same procedure and using equivalent amounts of the appropriate starting materials, there were also prepared:
6-[2-[4-(6-fluoro-1,2-benzisoxazol-3-yl)-1-piperidinyl]ethyl]-7-methyl-5H-thiazolo[3,2-a]pyrimidin-5-one; mp. 165.1° C. (compound 2);
3-[2-[4-(1,2-benzisoxazol-3-yl)-1-piperidinyl]ethyl]-2-methyl-4H-pyrido[1,2-a]pyrimidin-4-one; mp. 177.9° C. (compound 3);
3-[2-[4-(6-fluoro-1,2-benzisoxazol-3-yl)-1-piperidinyl]ethyl]-2,7-dimethyl-4H-pyrido[1,2-a]pyrimidin-4-one; mp. 186.9° C. (compound 4);
3-[2-[4-(1,2-benzisoxazol-3-yl)-1-piperidinyl]ethyl]-6,7,8,9-tetrahydro-2-methyl-4H-pyrido[1,2-a]pyrimidin-4-one; mp. 183.1° C. (compound 5);
3-[2-[4-(1,2-benzisothiazol-3-yl)-1-piperidinyl]ethyl]-2,4(1H,3H)-quinazolinedione monohydrochloride; mp. >300° C. (dec.) (compound 6);
3-[2-[4-(1,2-benzisothiazol-3-yl)-1-piperidinyl]ethyl]-6,7,8,9-tetrahydro-2-methyl-4H-pyrido[1,2-a]pyrimidin-4-one; mp. 145.7° C. (compound 7);
3-[2-[4-(6-hydroxy-1,2-benzisoxazol-3-yl)-1-piperidinyl]ethyl]-6,7,8,9-tetrahydro-2-methyl-4H-pyrido[1,2-a]pyrimidin-4-one; mp. 213.1° C. (compound 8).

In the similar manner are prepared
3-[2-[4-(5-methoxy-1,2-benzisoxazol-3-yl)-1-piperidinyl]ethyl]-2-methyl-4H-pyrido[1,2-a]pyrimidin-4-one (compound 9);
3-[2-[4-(6-fluoro-1,2-benzisoxazol-3-yl)-1-piperidinyl]ethyl]-2-methyl-4H-pyrido[1,2-a]pyrimidin-4-one (compound 10).

EXAMPLE 6

A mixture of 3.3 parts of 3-(2-chloroethyl)-2-methyl-4H-pyrido-[1,2-a]pyrimidin-4-one, 3.3 parts of 6-fluoro-3-(4-piperidinyl)-1,2-benzisoxazole, 8 parts of sodium carbonate, 1 part of potassium iodide and 120 parts of 4-methyl-2-pentanone was stirred and refluxed for 3 hours. The reaction mixture was cooled, water was added and the layers were separated. The organic phase was dried, filtered and evaporated. The residue was purified by column chromatography over silica gel using a mixture of trichloromethane and methanol (95:5 by volume) as eluent. The pure fractions were collected and the eluent was evaporated. The residue was crystallized from 4-methyl-2-pentanone, yielding 1.2 parts (19%) of 3-[2-[4-(6-fluoro-1,2-benzisoxazol-3-yl)-1-piperidinyl]ethyl]-2-methyl-4H-pyrido[1,2-a]pyrimidin-4-one; mp. 170.4° C. (compound 11).

EXAMPLE 7

A mixture of 6.75 parts of 6-fluoro-3-(4-piperidinyl)-1,2-benzisoxazole, 6.6 parts of 6-fluoro-3-(4-piperidinyl)-1,2-benzisoxazole, 10 parts of sodium hydrogen carbonate, 0.1 parts of potassium iodide and 90 parts of N,N-dimethyformamide was stirred and heated overnight at 100°–110° C. After cooling, the reaction mixture was poured into water. After stirring, the product was filtered off and crystallized from N,N-dimethylformamide, yielding 4.8 parts (39%) of 3-[2-[4-(6-fluoro-1,2-benzisoxazol-3-yl)-1-piperidinyl]ethyl]-2,4(1H,3H)-quinazolinedione; mp. 253.4° C. (compound 12).

EXAMPLE 8

A mixture of 7.4 parts of 6-(2-bromoethyl)-3,7-dimethyl-5H-thiazolo[3,2-a]pyrimidin-5-one monohydrobromide, 4.4 parts of 6-fluoro-3-(4-piperidinyl)-1,2-benzisoxazole, 10 parts of sodium carbonate and 90 parts of N,N-dimethylformamide was stirred overnight at 80°–85° C. After cooling, the reaction mixture was poured into water. The product was filtered off and purified by column chromatography over silica gel using a mixture of trichloromethane and methanol (95:5 by volume) as eluent. The pure fractions were collected and the eluent was evaporated. 2-Propanol was added to the residue. The product was filtered off and dried, yielding 5.3 parts (62%) of 6-[2-[4-(6-fluoro-1,2-benzisoxazol-3-yl)-1-piperidinyl]ethyl]-3,7-dimethyl-5H-thiazolo[3,2-a]pyrimidin-5-one; mp. 231.0° C. (compound 13).

In a similar manner there were also prepared:
6-[2-[4-(6-fluoro-1,2-benzisoxazol-3-yl)-1-piperidinyl]ethyl]-2,3-dihydro-7-methyl-5H-thiazolo[3,2-a]pyrimidin-5-one; mp. 135.0° C. (compound 14);
7-[2-[4-(6-fluoro-1,2-benzisoxazol-3-yl)-1-piperidinyl]ethyl]-3,4-dihydro-8-methyl-2H,6H-pyrimido[2,1-b][1,3]thiazin-6-one; mp. 169.3° C. (compound 15);
6-[2-[4-(1,2-benzisoxazol-3-yl)-1-piperidinyl]ethyl]-2,3-dihydro-7-methyl-5H-thiazolo[3,2-a]pyrimidin-5-one; mp. 154.5° C. (compound 16).
3-[2-[4-(6-fluoro-1,2-benzisothiazol-3-yl)-1-piperidinyl]ethyl]-6,7,8,9-tetrahydro-2-methyl-4H-pyrido[1,2-a]pyrimidin-4-one (compound 17);
3-[2-[4-(6-fluoro-1,2-benzisoxazol-3-yl)-1-piperidinyl]ethyl]-2,3-dihydro-2-thioxo-4(1H)-quinazolinone (compound 18).

(C) Pharmacological examples

The activity of the subject compounds as psychotic agents is evidenced by the experimental data obtained in at least one of two different test procedures, viz., the combined apomorphine-, tryptamine- and norepinephrine tests in rats and the apomorphine test in dogs. The tests are carried out following the procedures described hereafter and the experimental data are summarized in table 1.

EXAMPLE 9

The combined apomorphine (APO)-, tryptamine (TRY)- and norepinephrine (NOR) test in rats.

The experimental animals used in this test were adult male Wistar rats (weight 240±10 g). After an overnight fast, the animals were treated subcutaneously (1 ml/100 g) with an aqueous solution of the compound under investigation (time=zero) and put in isolated observation cages. Thirty minutes thereafter (time=30 minutes) 1.25 mg/kg of apomorphine hydrochloride (APO) was injected intravenously and the rats were observed over a 1 hour period for the presence or absence of the following apomorphine-induced phenomena; agitation and stereotypic chewing. At the end of this 1 hour period (time=90 minutes) the same animals were injected intravenously with 40 mg/kg of tryptamine (TRY) and the presence of the typical tryptamine-induced bilateral tonic seizures was noted. Two hours after pretreatment (time=120 minutes) finally, the same animals were challenged with 1.25 mg/kg intravenously of norephinephrine (NOR) and possible mortality was looked for up to 60 minutes later.

The table 1 gives the $ED_{50}$-value of a number of the compounds under consideration. As used herein, the $ED_{50}$-value represents the dose which protects 50% of the animals from apomorphine-, tryptamine- or norepinephrine-induced phenomena.

The apomorphine test in dogs (APO-dog).

The method used is described by P. A. J. Janssen and C. J. E. Niemegeers in Arzneim.-Forsch. (Drug Res.), 9, 765–767 (1959). The compounds listed in table 1 were administered subcutaneously to beagle dogs at different doses and the animals were challenged 1 hour thereafter with a standard dose of 0.31 mg/kg (subcutaneous) of apomorphine.

The table 1 gives the $ED_{50}$-values of a number of the compounds under consideration. As used herein, the $ED_{50}$ value represents the dose which protects 50% of the animals from emesis.

The compounds listed in table 1 are not given for the purpose of limiting the invention thereto but only to exemplify the useful pharmacological activities of all the compounds within the scope of formula (I).

TABLE 1

| Compound No. | $ED_{50}$(APO)—rat in mg/kg s.c. | $ED_{50}$(TRY)—rat in mg/kg s.c. | $ED_{50}$(NOR)—rat in mg/kg s.c. | $ED_{50}$(APO)—dog in mg/kg s.c. duration | |
|---|---|---|---|---|---|
| 1 | 0.08 | 0.08 | 0.16 | 1 h. | 0.008 |
|  |  |  |  | 2 h. | 0.005 |
|  |  |  |  | 4 h. | 0.015 |
|  |  |  |  | 8 h. | 0.018 |
|  |  |  |  | 16 h. | 0.02 |
| 2 | 0.02° | 0.005 | 0.31 | 1 h. | 0.004 |
|  |  |  |  | 4 h. | 0.008 |
|  |  |  |  | 16 h. | 0.16 |
| 11 | 0.02 | 0.01 | 0.16 | 1 h. | 0.015 |
|  |  |  |  | 4 h. | 0.03 |
| 13 | 0.02 | 0.02 | 0.08 | 1 h. | 0.015 |
|  |  |  |  | 4 h. | 0.06 |
| 14 | 0.02 | 0.005 | 0.31 | 1 h. | 0.004 |

TABLE 1-continued

| Compound No. | ED$_{50}$(APO)—rat in mg/kg s.c. | ED$_{50}$(TRY)—rat in mg/kg s.c. | ED$_{50}$(NOR)—rat in mg/kg s.c. | ED$_{50}$(APO)—dog in mg/kg s.c. duration | |
|---|---|---|---|---|---|
| 15 | 0.08 | 0.01 | 0.31 | 4 h. | 0.004 |
| | | | | 1 h. | 0.015 |
| | | | | 4 h. | 0.06 |

(D) Composition Examples

The following formulations exemplify typical pharmaceutical compositions in dosage unit form suitable for systemic administration to animal and human subjects in accordance with the instant invention.

"Active ingredient" (A.I.) as used throughout these examples relates to a compound of formula (I) or a pharmaceutically acceptable acid addition salt thereof.

EXAMPLE 10: ORAL DROPS

500 Grams of the A.I. was dissolved in 0.5 liters of 2-hydroxy-propanoic acid and 1.5 liters of the polyethylene glycol at 60°–80° C. After cooling to 30°–40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

EXAMPLE 11: ORAL SOLUTION

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

EXAMPLE 12: CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

EXAMPLE 13: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 milliliters of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 milligrams of the active ingredient.

Coating

To a solution of 10 grams methyl cellulose (Methocel 60 HG ®) in 75 milliliters of denatured ethanol there was added a solution of 5 grams of ethyl cellulose (Ethocel 22 cps ®) in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109 ®) and the whole was homogenated.

The tablet cores were coated with the thus obtained mixture in a coating apparatus.

EXAMPLE 14: INJECTABLE SOLUTION 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 grams propylene glycol and 4 grams of the A.I..

The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

EXAMPLE 15: SUPPOSITORIES

3 Grams A.I. was dissolved in a solution of 3 grams 2,3-dihydroxybutanedioic acid in 25 milliliters polyethylene glycol 400. 12 Grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°–38° C. to form 100 suppositories each containing 30 milligrams of the active ingredient.

We claim:

1. A chemical compound having the formula or a pharmaceutically acceptable acid addition salt thereof, wherein R is hydrogen or $C_{1-6}$ alkyl;

$R^1$ and $R^2$ are each independently members selected from the group consisting of hydrogen, halo, hydroxy, $C_{1-6}$ alkyloxy and $C_{1-6}$ alkyl;

X is O or S;

Alk is $C_{1-4}$ alkanediyl; and

Q is a radical of formula

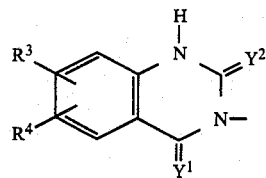

(a)

wherein $Y^1$ and $Y^2$ are each independently O or S;
$R^3$ is a member selected from the group consisting of hydrogen, halo, $C_{1-6}$ alkyl, $C_{1-6}$ alkyloxy, trifluoromethyl, nitro, cyano, hydroxy, ($C_{1-10}$ alkylcarbonyl)oxy, amino, mono- and di($C_{1-6}$ alkyl)amino, ($C_{1-10}$ alkylcarbonyl)amino, phenylmethoxy and azido;
$R^4$ is hydrogen or halo; or a radical of formula

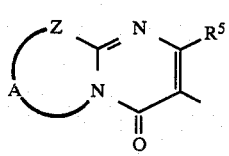

(b)

wherein $R^5$ is hydrogen or $C_{1-6}$ alkyl;
Z is —S—, —CH$_2$— or —CR$^6$=CR$^7$—; said $R^6$ and $R^7$ being each independently hydrogen or $C_{1-6}$ alkyl; and
A is a bivalent radical —CH$_2$—CH$_2$—, —CH$_2$—CH$_2$—CH$_2$— or —CR$^8$=CR$^9$—, said $R^8$ and $R^9$ being each independently hydrogen, halo, amino or $C_{1-6}$ alkyl.

2. A chemical compound according to claim 1, wherein Q is a radical of formula (a) wherein $R^3$ is hydrogen, halo, $C_{1-6}$ alkyl, $C_{1-6}$ alkyloxy, trifluoromethyl, hydroxy, amino or azido and $R^4$ is hydrogen; or Q is a radical of formula (b) wherein $R^5$ is $C_{1-6}$ alkyl and A is a bivalent radical —CH$_2$—CH$_2$—, —CH$_2$—CH$_2$—CH$_2$— or —CR$^8$=CR$^9$— wherein $R^8$ and $R^9$ are each independently hydrogen or $C_{1-6}$ alkyl.

3. A chemical compound according to claim 2, wherein R is hydrogen, $R^1$ is hydrogen or halo and $R^2$ is hydrogen, halo, hydroxy or $C_{1-6}$ alkyloxy.

4. A chemical compound according to claim 3, wherein Q is a radical of formula (a) wherein $R^3$ is hydrogen, halo or methyl and $Y^1$ is O; or Q is a radical of formula (b) wherein —Z—A— is —S—CH$_2$—CH$_2$—, —S—(CH$_2$)$_3$—, —S—CR$^8$=CR$^9$— wherein $R^8$ and $R^9$ are each independently hydrogen or methyl, —CH=CH—CR$^8$=CR$^9$— wherein $R^8$ and $R^9$ are each independently hydrogen or methyl, or —CH$_2$—CH$_2$—CH$_2$—CH$_2$—.

5. A chemical compound according to claim 4, wherein $R^1$ is hydrogen, and $R^2$ is hydrogen, halo, hydroxy or methoxy.

6. A chemical compound according to claim 1 wherein the compound is 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one or 3-[2-[4-(6-fluoro-1,2-benzisoxazol-3-yl)-1-piperidinyl]ethyl]-2-methyl-4H-pyrido[1,2-a]pyrimidin-4-one.

7. A pharmaceutical composition for treating psychotic diseases, comprising an inert carrier and as an active ingredient a pharmaceutically effective amount of a chemical compound having the formula

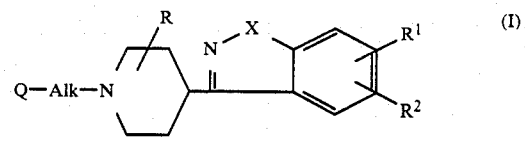

(I)

or a pharmaceutically acceptable acid addition salt thereof, wherein
R is hydrogen or $C_{1-6}$ alkyl;
$R^1$ and $R^2$ are each independently members selected from the group consisting of hydrogen, halo, hydroxy, $C_{1-6}$ alkyloxy and $C_{1-6}$ alkyl;
X is O or S;
Alk is $C_{1-4}$ alkanediyl; and
Q is a radical of formula

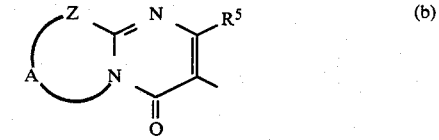

(a)

wherein $Y^1$ and $Y^2$ are each independently O or S;
$R^3$ is a member selected from the group consisting of hydrogen, halo, $C_{1-6}$ alkyl, $C_{1-6}$ alkyloxy, trifluoromethyl, nitro, cyano, hydroxy, ($C_{1-10}$ alkylcarbonyl)oxy, amino, mono- and di($C_{1-6}$ alkyl)amino, ($C_{1-10}$ alkylcarbonyl)amino, phenylmethoxy and azido;
$R^4$ is hydrogen or halo; or
a radical of formula

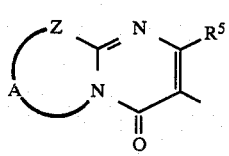

(b)

wherein $R^5$ is hydrogen or $C_{1-6}$ alkyl;
Z is —S—, —CH$_2$— or —CR$^6$=CR$^7$—; said $R^6$ and $R^7$ being each independently hydrogen or $C_{1-6}$ alkyl; and
A is a bivalent radical —CH$_2$—CH$_2$—, —CH$_2$—CH$_2$—CH$_2$— or —CR$^8$=CR$^9$—, said $R^8$ and $R^9$ being each independently hydrogen, halo, amino or $C_{1-6}$ alkyl.

8. A pharmaceutical composition according to claim 7 wherein Q is a radical of formula (a) wherein $R^3$ is hydrogen, halo, $C_{1-6}$ alkyl, $C_{1-6}$ alkyloxy, trifluoromethyl, hydroxy, amino or azido and $R^4$ is hydrogen; or Q is a radical of formula (b) wherein $R^5$ is $C_{1-6}$ alkyl and A is a bivalent radical —CH$_2$—CH$_2$—, —CH$_2$—CH$_2$—CH$_2$— or —CR$^8$=CR$^9$— wherein $R^8$ and $R^9$ are each independently hydrogen or $C_{1-6}$ alkyl.

9. A pharmaceutical composition according to claim 8 wherein R is hydrogen, $R^1$ is hydrogen or halo and $R^2$ is hydrogen, halo, hydroxy or $C_{1-6}$ alkyloxy.

10. A pharmaceutical composition according to claim 9 wherein Q is a radical of formula (a) wherein $R^3$ is hydrogen, halo or methyl and $Y^1$ is O; or Q is a radical of formula (b) wherein —Z—A— is —S—CH$_2$—CH$_2$—, —S—(CH$_2$)$_3$—, —S—CR$^8$=CR$^9$— wherein $R^8$ and $R^9$ are each independently hydrogen or methyl, —CH=CH—CR$^8$=CR$^9$— wherein R$^8$ and R$^9$ are each independently hydrogen or methyl, or —CH$_2$—CH$_2$—CH$_2$—CH$_2$—.

11. A pharmaceutical composition according to claim 10 wherein R$^1$ is hydrogen, and R$^2$ is hydrogen, halo, hydroxy or methoxy.

12. A pharmaceutical composition according to claim 7 wherein the compound is 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one or 3-[2-[4-(6-fluoro-1,2-benzisoxazol-3-yl)-1-piperidinyl]ethyl]-2-methyl-4H-pyrido[1,2-a]pyrimidin-4-one.

13. A method of treating warm-blooded animals suffering from psychotic diseases which comprises the administration thereto of a pharmaceutically effective amount of a chemical compound having the formula

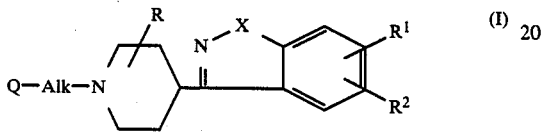

or a pharmaceutical acceptable acid addition salt thereof, wherein

R is hydrogen or C$_{1-6}$ alkyl;

R$^1$ and R$^2$ are each independently members selected from the group consisting of hydrogen, halo, hydroxy, C$_{1-6}$ alkyloxy and C$_{1-6}$ alkyl;

X is O or S;

Alk is C$_{1-4}$ alkanediyl; and

Q is a radical of formula

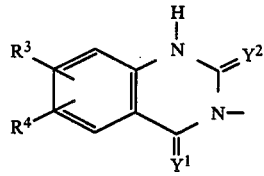

wherein Y$^1$ and Y$^2$ are each independently O or S;

R$^3$ is a member selected from the group consisting of hydrogen, halo, C$_{1-6}$ alkyl, C$_{1-6}$ alkyloxy, trifluoromethyl, nitro, cyano, hydroxy, (C$_{1-10}$ alkylcarbonyl)oxy, amino, mono- and di(C$_{1-6}$ alkyl)amino, (C$_{1-10}$ alkylcarbonyl)amino, phenylmethoxy and azido;

R$^4$ is hydrogen or halo; or a radical of formula

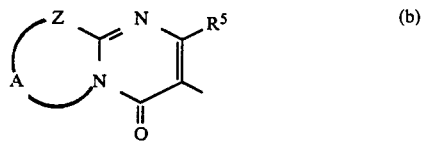

wherein R$^5$ is hydrogen or C$_{1-6}$ alkyl;

Z is —S—, —CH$_2$— or —CR$^6$=CR$^7$—; said R$^6$ and R$^7$ being each independently hydrogen or C$_{1-6}$ alkyl; and A is a bivalent radical —CH$_2$—CH$_2$—, —CH$_2$—CH$_2$—CH$_2$— or —CR$^8$=CR$^9$—; said R$^8$ and R$^9$ being each independently hydrogen, halo, amino or C$_{1-6}$ alkyl.

14. A method according to claim 13 wherein Q is a radical of formula (a) wherein R$^3$ is hydrogen, halo, C$_{1-6}$ alkyl, C$_{1-6}$ alkyloxy, trifluoromethyl, hydroxy, amino or azido and R$^4$ is hydrogen; or Q is a radical of formula (b) wherein R$^5$ is C$_{1-6}$ alkyl and A is a bivalent radical —CH$_2$—CH$_2$—, —CH$_2$—CH$_2$—CH$_2$— or —CR$^8$=CR$^9$— wherein R$^8$ and R$^9$ are each independently hydrogen or C$_{1-6}$ alkyl.

15. A method according to claim 14 wherein R is hydrogen, R$^1$ is hydrogen or halo and R$^2$ is hydrogen, halo, hydroxy or C$_{1-6}$ alkyloxy.

16. A method according to claim 15 wherein Q is a radical of formula (a) wherein R$^3$ is hydrogen, halo or methyl and Y$^1$ is O; or Q is a radical of formula (b) wherein —Z—A— is —S—CH$_2$—CH$_2$—, —S—(CH$_2$)$_3$—, —S—CR$^8$=CR$^9$— wherein R$^8$ and R$^9$ are each independently hydrogen or methyl, —CH=CH—CR$^8$=CR$^9$— wherein R$^8$ and R$^9$ are each independently hydrogen or methyl, or —CH$_2$—CH$_2$—CH$_2$—CH$_2$—.

17. A method according to claim 16 wherein R$^1$ is hydrogen, and R$^2$ is hydrogen, halo, hydroxy or methoxy.

18. A method according to claim 13 wherein the compound is 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one or 3-[2-[4-(6-fluoro-1,2-benzisoxazol-3-yl)-1-piperidinyl]ethyl]-2-methyl-4H-pyrido[1,2-a]pyrimidin-4-one.

* * * * *

UNITED STATES PATENT AND TRADEMARK OFFICE

CERTIFICATE EXTENDING PATENT TERM
UNDER 35 U.S.C. § 156

PATENT NO.    : 4,804,663

DATED         : February 14, 1989

INVENTOR(S)   : Ludo E.J. Kennis et al.

PATENT OWNER  : Janssen Pharmaceutica N.V.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

683 DAYS with all rights pertaining thereto as provided by 35 U.S.C. § 156(b).

I have caused the seal of the Patent and Trademark Office to be affixed this 23rd day of January 1996.

Bruce A. Lehman
Assistant Secretary of Commerce and
Commissioner of Patents and Trademarks